United States Patent [19]
Partridge et al.

[11] Patent Number: 4,652,405
[45] Date of Patent: Mar. 24, 1987

[54] SYNTHESIS OF
1α,25-DIHYDROXY-24R-FLUORO-CHOLECALCIFEROL AND
1α,25-DIHYDROXY-24S-FLUORO-CHOLECALCIFEROL

[75] Inventors: John J. Partridge, Upper Montclair; Shian-Jan Shiuey, Nutley; Milan R. Uskokovic, Upper Montclair, all of N.J.

[73] Assignee: Hoffman-La Roche Inc., Nutley, N.J.

[21] Appl. No.: 405,854

[22] Filed: Aug. 6, 1982

Related U.S. Application Data

[63] Continuation-in-part of Ser. No. 297,446, Aug. 28, 1981, abandoned.

[51] Int. Cl.⁴ .................................................. C07J 9/00
[52] U.S. Cl. .............................. 260/397.1; 260/397.2; 514/167
[58] Field of Search ............................ 260/397.1, 397.2

[56] References Cited

U.S. PATENT DOCUMENTS 3,847,955 11/1974 DeLuca .............................. 260/397.2
4,229,357 10/1980 DeLuca et al. ..................... 260/397.2
4,428,946 1/1984 DeLuca et al. ..................... 424/236

Primary Examiner—Elbert L. Roberts
Attorney, Agent, or Firm—Jon S. Saxe; Bernard S. Leon; Mathew Boxer

[57] ABSTRACT

1α,25-Dihydroxy-24R-fluorocholecalciferol and 1α,25-dihydroxy-24S-fluorocholecalciferol, analogs of 1α,25-dihydroxy-cholecalciferol which is physiologically the most active metabolite of vitamin D₃, are synthesized in a multistep process from the known substance 1α,3β-dihydroxyandrost-5-en-17-one. The new analogs are characterized by the ability to increase intestinal calcium transport, increase serum calcium and phosphate concentrations and to increase the deposition of these minerals in bones. These compounds will find a ready application as substitutes for natural 1α,25-dihydroxy-cholecalciferol in the treatment of disease states characterized by metabolic calcium and phosphate deficiencies. Exemplary of such disease states are the following: osteosclerosis, anticonvulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, hypophosphatemic VDRR, vitamin D-dependent rickets, sarcoidosis, glucocorticoid antagonism, malabsorption syndrome, steatorrhea, tropical sprue, idiopathic hypercalcemia and milk fever.

47 Claims, No Drawings

SYNTHESIS OF 1α,25-DIHYDROXY-24R-FLUOROCHOLECALCIFEROL AND 1α,25-DIHYDROXY-24S-FLUOROCHOLECALCIFEROL

BACKGROUND OF THE INVENTION

This invention relates to 24R- and 24S-fluoro analogs of 1α,25-dihydroxycholecalciferol.

Vitamin $D_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective, vitamin $D_3$ must be converted in vivo to its hydroxylated forms. For example, the vitamin is first hydroxylated in the liver to form 25-hydroxy-vitamin $D_3$ and is further hydroxylated in the kidney to produce 1α,25-dihydroxy vitamin $D_3$ or 24,25-dihydroxy vitamin $D_3$. The 1α-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and retaining calcium in the kidneys.

Since the discovery of biologically active metabolites of vitamin D there has been much interest in the preparation of structural analogs of these metabolites, because such compounds may represent useful therapeutic agents for the treatment of diseases resulting from calcium metabolism disorders.

SUMMARY OF THE INVENTION

The present invention relates to a process and intermediates for preparing 1α,25-dihydroxy-24R-fluorocholecalciferol and 1α,25-dihydroxy-24S-fluorocholecalciferol from the readily available 1α,3β-dihydroxyandrost-5-en-17-one, which is made by a known microbiological process from 3β-hydroxyandrost-5-en-17-one [R. M. Dodson, A. H. Goldkamp and R. D. Muir, *J. Amer. Chem. Soc.*, 82, 4026 (1960)].

These compounds will find a ready application as substitutes for natural 1α,25-dihydroxycholecalciferol in the treatment of disease states characterized by metabolic calcium and phosphate deficiencies. Exemplary of such disease states are the following: osteomalacia, osteoporosis, rickets, osteitis fibrosa cystica, renal osteodystrophy, osteosclerosis, anticonvulsant treatment, osteopenia, fibrogenesis imperfecta ossium, secondary hyperparathyrodism, hypoparathyroidism, hyperparathyroidism, cirrhosis, obstructive jaundice, drug induced metabolism, medullary carcinoma, chronic renal disease, hypophosphatemic VDRR, vitamin D-dependent rickets, sarcoidosis, glucocorticoid antagonism, malabsorption syndrome, steatorrhea, tropical sprue, idiopathic hyper calcemia and milk fever.

The synthesis involves as key steps the introduction of the properly substituted 6-carbon moieties by alkylation to give either the 24R- or 24S-fluorinated side chains, the hydrogenolysis sequence to form the desired 20R-methyl group, the formation of a specific 5,7-diene and the final photolysis-thermolysis sequence affording either 1α,25-dihydroxy-24R-fluorocholecalciferol or 1α,25-dihydroxy-24S-fluorocholecalciferol.

DETAILED DESCRIPTION OF THE INVENTION

As used throughout the specification and the appended claims, the term "lower alkyl" refers to a monovalent substituent consisting solely of carbon and hydrogen of from 1 to 8 carbon atoms which may be straight or branched-chain. Examples of lower alkyl groups are methyl, ethyl, n-propyl, i-propyl, tert.-butyl, hexyl, heptyl, octyl and so forth. The term "lower alkylene group" refers to a divalent substituent consisting solely of carbon and hydrogen of from 1 to 8 carbon atoms which may be straight or branched-chain and whose free valences are attached to two distinct groups. Examples of alkylene groups are methylene, ethylene, propylene and so forth. The term "lower alkoxy" refers to a lower alkyl group attached to the remainder of the molecule by oxygen.

Examples of alkoxy groups are methoxy, ethoxy, isopropoxy, tert.-butoxy and so forth. The term "phenyl alkoxy" refers to an alkoxy group which is substituted by a phenyl ring. Examples of phenyl alkoxy groups are benzyloxy, 2-phenylethoxy, 4-phenylbutoxy and so forth. The term "alkanoyloxy group" refers to the residue of an alkylcarboxylic acid formed by removal of the hydrogen from the hydroxyl portion of the carboxyl group. Examples of alkanoyloxy groups are formyloxy, acetoxy, butyryloxy, hexanoyloxy and so forth. The term "substituted" as applied to "phenyl" refers to phenyl which is sibustituted with one or more of the following groups: alkyl, halogen (i.e., fluorine, chlorine, bromine or iodine), nitro, cyano, trifluoromethyl and so forth. The term "alkanol" refers to a compound derived by protonation of the oxygen atom of an alkoxy group. Examples of alkanols are methanol, ethanol, 2-propanol, 2-methyl-2-propanol and the like.

In the formulas presented herein, the various substituents are illustrated as joined to the steroid nucleus by one of these notations: a solid line (—) indicating a substituent which is in the β-orientation (i.e., above the plane of the molecule), a dotted line (- - -) indicating a substituent which is in the α-orientation (i.e., below the plane of the molecule), or a wavy line (∿) indicating a substituent which may be in the α- or β-orientation. The formulas have all been drawn to show the compounds in their absolute stereochemical configurations. Since the starting materials are derived from a naturally occurring steroid, the products exist in the single absolute configuration depicted herein. However, the processes of the present invention are intended to apply as well to the synthesis of steroids of the "unnatural" and racemic series, i.e., the enantiomers of the compounds depicted herein and mixtures of both. Thus, one may begin the synthesis utilizing "unnatural" or racemic starting materials to prepare "unnatural" or racemic products, respectively.

The Greek letter xi (ξ) in the name of a vitamin $D_3$ intermediate or metabolite indicates that the stereochemistry of the substituent to which is refers is undefined or that the product consists of a mixture of compounds epimeric at the designated position.

The nomenclature adopted to define absolute configuration of substituents bound to carbon atom 24 of the steroid nucleus is described in the *Journal of Organic Chemistry*, 34, 2849 (1970) under the title "IUPAC Tentative Rules for the Nomenclature of Organic Chemistry. Section E. Fundamental Stereochemistry."

In the first step in the synthetic sequence, a compound of formula I

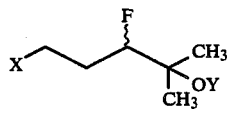

wherein X is iodo, bromo, chloro, lower alkylsulfonyloxy, phenylsulfonyloxy, or substituted phenylsulfonyloxy, F is fluoro, and Y is a group of the formula

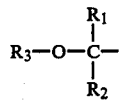

wherein $R_1$ is hydrogen or lower alkyl, $R_2$ and $R_3$ each taken independently are lower alkyl and $R_2$ and $R_3$ taken together are lower alkylene of from 3 to 6 carbons and the absolute configuration at the carbon bearing fluorine is either R or S or a R,S-mixture is reacted with a metallated pregn-5-en-21-oic acid ester of formula II

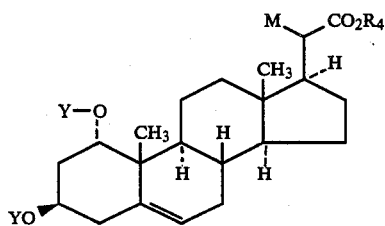

wherein M is lithium, sodium, potassium, magnesium/2 or zinc/2, where $R_4$ is lower alkyl, phenyl, and substituted phenyl and where Y is as above according to the method of J. Wicha and K. Bal [J.Chem.Soc., Perkin Trans.I, 1282 (1978)] to give the corresponding alkylated compound III

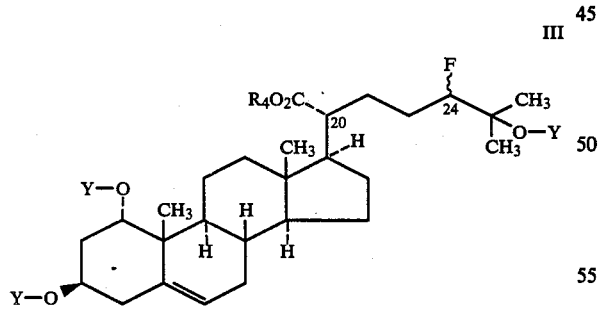

wherein $R_4$, F and Y are as above and the absolute configuration at C-24 is R or S or a R,S-mixture which contains the side chain bearing the desired 20R-absolute stereochemistry and all of the carbons of the cholecalciferol skeleton and which also contains a fluorine at the 24-position and protected hydroxy groups at the 1α, 3β, and 25-positions.

The metallated pregn-5-en-21-oic acid ester of formula II is prepared from pregn-5-en-21-oic acid ester IV

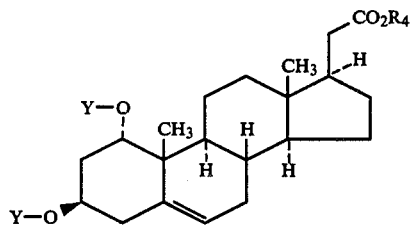

wherein $R_4$ and Y are as above by treatment with an appropriate organometallic reagent. For example, the lithium salt, may be formed by reaction of the compound of formula IV with, for example, lithium diisopropylamide. The sodium salt may be formed by reaction of the compound of formula IV with, for example, sodium hexamethyldisilazane. The potassium salt may be formed by reaction with the compound of formula IV with, for example, potassium hydride.

As mentioned above, the metallated pregn-5-en-21-oic acid ester of formula II is reacted with the halide or sulfonate ester of formula I to afford the alkylated compound of formula III. The aforementioned reaction may be carried out in aprotic inert solvents such as, for example, ethers, e.g. diethyl ether, tetrahydrofuran, dimethoxyethane, dioxane and so forth; amides, e.g. hexamethylphosphoramide and so forth. Preferred solvents for this purpose are tetrahydrofuran and hexamethylphosphoramide. The use of tetrahydrofuran-hexamethylphosphoramide mixtures is particularly preferred.

The alkylation reactions between compounds of formulas I and II are conveniently carried out at a temperature between −78° C. and 60° C. Most preferably, the alkylation reaction is conducted between a temperature of about −40° C. to 0° C. The desired alkylation product of formula III, containing the desired 20R-absolute configuration, can be isolated by the usual chemical and physical means such as chromatography and in this manner can be separated from any undesired impurities such as starting materials of formulas I and IV.

In the next step, the alkylated compound of formula III is reduced to the alcohol of formula V

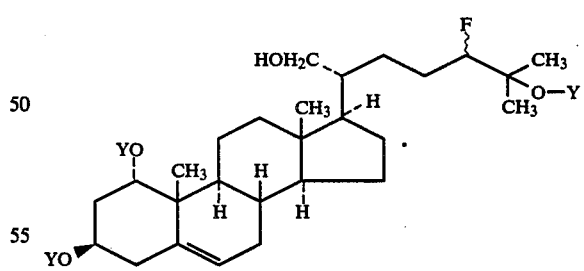

wherein Y and F are as above and the absolute configuration at C-24 is R or S or a R,S mixture by reduction of the ester grouping with a complex metal hydride reducing agent. Suitable complex metal hydride reducing agents for this purpose include alkali metal aluminum hydrides such as lithium aluminum hydride; mono-, di- or tri-(lower alkoxy)alkali metal aluminum hydrides such as, for example, lithium tris(tert.-butoxy)aluminum hydride; mono-, di- or tri(lower alkoxy lower alkoxy)alkali metal aluminum hydrides such as, for example, sodium bis(2-methoxyethoxy)aluminum hydride; di(- lower alkyl)aluminum hydrides such as, for example, diisobutyl aluminum hydride; and so forth. A particularly preferred complex metal reducing agent for this purpose is lithium aluminum hydride. Suitable solvents for this reduction include ethers such as diethyl ether, tetrahydrofuran, dimethoxyethane, and dioxane. The reduction is conveniently carried out at a temperature between about 0° C. and 100° C., most preferably between about 35° C. and 70° C.

The alcohol of formula V is subsequently converted in the next reaction step to the halide or sulfonate ester of formula VI

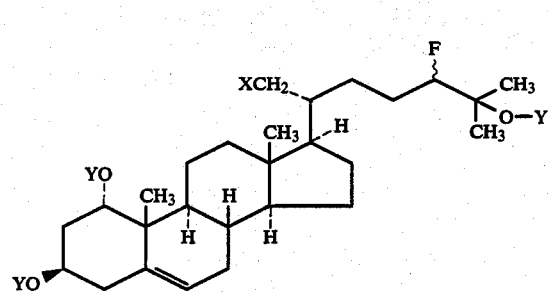

VI wherein X is iodo, bromo, chloro, lower alkylsulfonyloxy, phenylsulfonyloxy, or substituted phenylsulfonyloxy, Y and F are as above, and the absolute configuration at C-24 is R or S, or a R,S mixture.

To prepare a compound of formula VI where X is a substituted sulfonyloxy group, one would react the compound of formula V with a properly substituted sulfonyl halide in the presence of a base according to methods known per se. The preparation of compounds of formula VI which X is iodo, bromo or chloro, can be accomplished either by direct conversion of the alcohol of formula V to the desired halo group by means of a halogenating agent such as, for example, phosphorus tribromide, according to methods known per se, or by reaction of one of the sulfonate esters of formula VI with a halide ion containing compound. For example, the compound of formula VI where X is tosyloxy may be reacted with an alkali metal bromide or iodide, for example, potassium bromide or potassium iodide, to afford the compound of formula VI where X is bromo or iodo, respectively. All of these interconnections to prepare the compounds of formula VI are standard in the art for the preparation of primary alkyl halides and sulfonate esters from primary alcohols.

In the next step the compound of formula VI is converted to the compound of formula VII

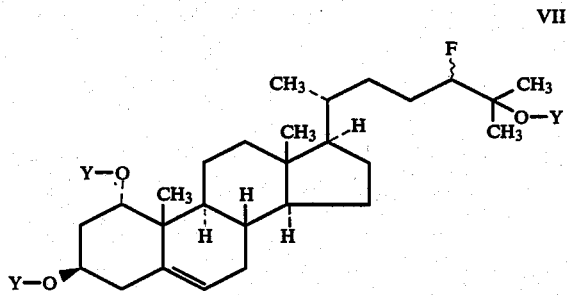

VII wherein Y and F are as above and the absolute configuration at C-24 is R or S, or a R,S-mixture with a complex metal hydride reducing agent. Suitable complex metal hydride reducing agents for this purpose include metal aluminum hydrides such as lithium aluminum hydride; mono-, di-, or tri(lower alkoxy)alkali metal aluminum hydride such as, for example, lithium tri(tert.-butoxy)aluminum hydride; mono-, di-, or tri(lower alkoxy lower alkoxy)aluminum metal hydrides such as for example, sodium bis(2-methoxyethoxy)aluminum hydride; di(lower alkyl)aluminum hydrides such as for example, diisobutylaluminum hydride; and so forth. A particularly preferred complex metal hydride reducing agent for this purpose is lithium aluminum hydride. Suitable solvents for the reduction include ethers such as diethyl ether, tetrahydrofuran, dimethoxyethane, and dioxane. The reduction is normally carried out at a temperature between about room temperature and about 100° C., most preferably between about 40° C. and 80° C. Other suitable reducing agents, particularly when A is iodo or bromo in the compound of formula VI, are alkali metal cyanoborohydrides such as, for example, sodium cyanoborohydride(sodium cyanotrihydroborate); tri(lower alkyl)tin hydrides such as tri-n-butyltin hydride; and tri(aryl)tin hydrides such as triphenyltin hydride; and so forth. A particularly preferred complex metal reducing agent is tri-n-butyltin hydride. Suitable solvents for the reduction include ethers such as diethyl ether, tetrahydrofuran, dimethoxyethane, and dioxane. The reduction is normally carried out at a temperature between about $-20°$ C. and 80° C., most preferably between about 0° C. and 40° C.

The compound of formula VII can be converted to the $1\alpha,25$-dihydroxy-24-fluorocholesterol of formula VIII

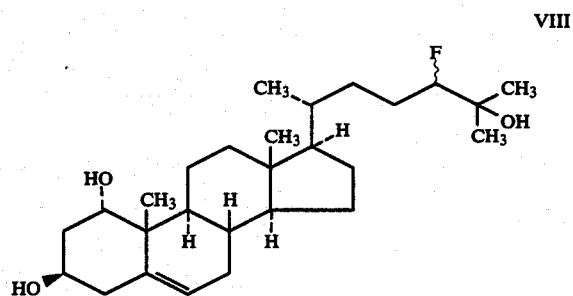

VIII wherein F is as above and the absolute configuration at C-24 is R or S, or a R,S-mixture by removal of the protecting groups Y of the compound of formula VII with a strong acid in a protic solvent. Suitable strong acids for this purpose include mineral acids such as hydrochloric or sulfuric acid; and organic sulfonic acids such as p-toluenesulfonic acid. Suitable solvents include alcohols such as methanol and ethanol, and water containing a miscible co-solvent to help solubilize the organic reactants, for example, ethers such as tetrahydrofuran or dimethoxyethane; or a ketone such as acetone. It is preferable to carry out the removal of alcohol protecting groups Y of formula VII at a temperature between about $-10°$ C. and about 80° C., most preferably between about 0° C. and 40° C.

The cholesterol of formula VIII is then alkanoylated to the $1\alpha,3\beta$-dialkanoate compounds of formula IX

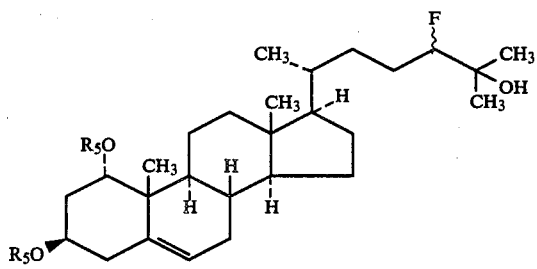

IX wherein $R_5$ is lower alkanoyl, F is as above, and the absolute configuration at C-24 is R or S, or a R,S-mixture by methods well known in the art. For example, to acetylate the 1α- and 3β- hydroxy groups of compounds of the formula VIII, one employs acetic anhydride and pyridine at a temperature of about 25° C.

The compound of formula IX is allylically halogenated to a mixture of 7α- and 7β-halocholesterols of the formula X

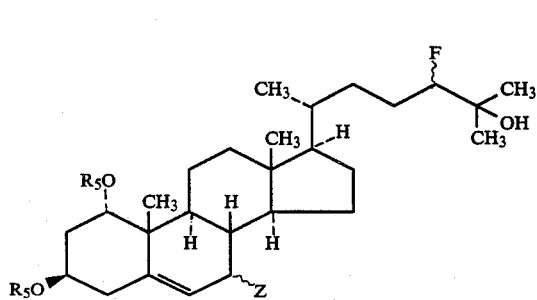

X wherein $R_5$ and F are as above, Z is iodo, bromo or chloro, and the absolute configuration at C-24 is R or S or a R,S mixture.

The halogenation reaction is accomplished using a suitable halogenation agent such as 1,3-dibromo-5,5-dimethylhydantoin, N-chlorosuccinimide, N-bromosuccinimide, N-bromoacetamide and the like, dissolved in a saturated aliphatic hydrocarbon or halocarbon, such as hexane or carbon tetrachloride, in the presence of an acid scavenger, such as sodium bicarbonate or sodium carbonate at the boiling point of the reaction medium to give a mixture of 7α- and 7β-halocholesterols, which is used in the following dehydrohalogenation step without separation of the 7β-halo-isomer from the predominant 7α-isomer.

The 7α- and 7β-halocholesterol mixture of formula X is converted to the steroid 5,7-diene of formula XI

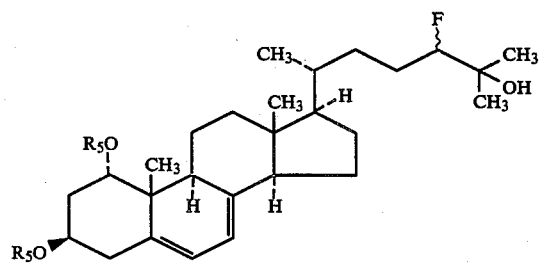

XI wherein $R_5$ and F are as above and the absolute configuration at C-24 is R or S or a R,S-mixture by a dehydrohalogenation step. The dehydrohalogenation of the crude mixture of 7α- and 7β-halocholesterols is affected by heteroaromatic and aliphatic tertiary amines are pyridines and alkylated pyridines such as picolines, lutidines and collidines; suitable aliphatic tertiary amines are triethylamine, tripropylamine, 1,5-diazabicyclo(4.3.0)non-5-ene, 1,4-diazabicyclo(2.2.2)octane and the like; s-collidine being preferred. Trialkylphosphites are also useful in the dehydrohalogenation step. Suitable inert organic solvents include aromatic and aliphatic organic solvents, such as benzene, toluene, xylene, decalin and the like. Xylene is the preferred solvent. The reaction proceeds readily at temperatures from about 50° C. to the reflux temperature of the reaction medium, most readily at the reflux temperature of the solvent system. The desired steroid 5,7-diene of formula XI can be isolated by the usual chemical and physical means such as chromatography and in this manner can be separated from any undesired impurities such as the 4,6-diene of formula XII

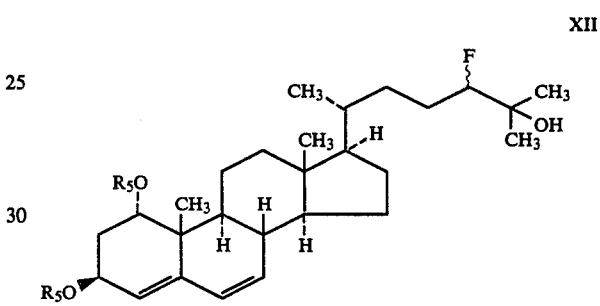

XII wherein $R_5$ and F are as above and the absolute configuration at C-24 is R or S or a R,S-mixture.

In a key reaction, the steroid 5,7-diene of formula XI is converted into the precholecalciferol 1α,3β-dialkanoate of formula XIII

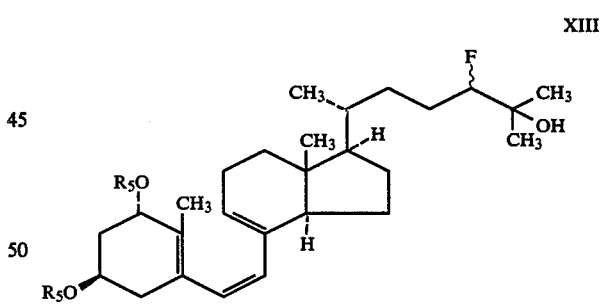

XIII wherein $R_5$ and F are as above and the absolute configuration at C-24 is R or S or a R,S-mixture by irradiation under an inert atmosphere by means of a mercury lamp equipped with a glass cooling finger at a temperature of about −40° C. to about +25° C., −5° C. being the preferred irradiation temperature for the period of time necessary to effect about 50% conversion of the starting material. Suitable inert atmospheres include nitrogen, helium, argon, and the like. Suitable source of irradiation energy include high and low pressure mercury, xenon-mercury, and thallium-mercury lamps. High pressure mercury lamps are preferred. A 450 W Hanovia high pressure mercury lamp is the most preferred source of irradiation energy. Suitable inert organic solvent systems for the irradiation include mixtures of saturated aliphatic hydrocarbons, such as pentane, hexane, isooctane and the like and ethereal solvents such as diethyl ether, dimethoxyethane, tetrahydrofuran, dioxane and the like. Preferred mixtures contain hexane and tetrahydrofuran.

Upon completion of the irradiation, the solvents are removed by evaporation and the residue is separated into the pure precholecalciferol 1α,3β-dialkanoate of formula XIII and pure unchanged steroid 5,7-diene of formula XI on a high performance liquid chromatography column using a solid absorbent and an inert organic eluant. Suitable organic eluants for the separation step include mixtures of hydrocarbons, such as n-hexane, isooctane, benzene, toluene and the like and esters such as ethyl acetate, ethyl benzoate and the like. Suitable solid absorbants include Porasil, Corasil, Biosil, Zorbax, Zorbax-Sil, Sil-X and the like. A Waters Associates Chromatograph Model 202 using an 8-foot by ⅜ inch Porasil A column and a mixture of n-hexane/ethyl acetate as the eluant is the preferred high performance liquid chromatographic system.

Unchanged 5,7-diene of formula XI is recycled through the irradiation process to obtain additional quantities of pure precholecalciferol 1α,3β-dialkanoate of formula XIII, thereby rendering this crucial step of the process and the overall process highly efficient in comparison with related processes previously disclosed, for example, by D. H. R. Barton, et. al., *J. Chem. Soc. Chem. Comm.*, 203 (1974) and by H. F. DeLuca, et. al., *Tetrahedron Lett.*, 4417 (1972).

The precholecalciferol 1α,3β-dialkanoate of formula XIII is saponified to the precholecalciferol of formula XIV

XIV

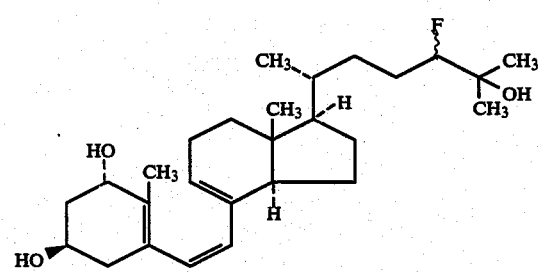

wherein F is as above and the absolute configuration at C-24 is R or S or a R,S-mixture. The saponification of the compound of formula XIII is conducted by treatment with strong bases in protic solvents. Suitable bases include alkali and alkaline earth hydroxides, alkoxides such as methoxides, ethoxides and the like. Potassium hydroxide is most preferred. Suitable solvents include alcohols such as methanol and ethanol, and water containing a miscible co-solvent to help solubilize the organic reactants, for example, an ether such as tetrahydrofuran, or dimethoxyethane. Methanol is most preferred. It is preferrable to carry out the removal of the alkanoyl protecting groups R₅ of formula XIII at a temperature between about −20° C. and about 60° C., most preferably between about −5° C. and 30° C. It is also preferable to perform the saponification under an inert atmosphere of nitrogen, argon, and the like.

The final step in the main sequence involves the thermal isomerization of precholecalciferol of formula XIV to the 1α,25-dihydroxy-24ξ-fluorocholecalciferol of formula XV

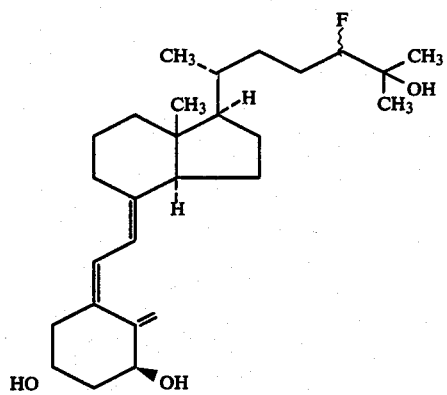

wherein F is as above and the absolute configuration at C-24 is R or S or a R,S-mixture by heating the precholecalciferol of formula XIV in an inert solvent such as the ethers, dioxane, tetrahydrofuran, dimethoxyethane and the like; the aromatic hydrocarbons such as, benzene, toluene and the like, under an inert atmosphere, such as argon, helium, and the like, by methods well known in the art. See for example, D. H. R. Barton, e. al., *J. Amer. Chem. Soc.*, 98, 2748 (1973).

The preparation of a compound of formula I with the R-absolute configuration at the carbon bearing fluorine is shown in the Scheme below beginning with the known (−)-2S-hydroxy-4-butyrolactone (1) [J. W. E. Glattfield and F. V. Sander, *J. Amer. Chem. Soc.*, 43, 2675 (1921)].

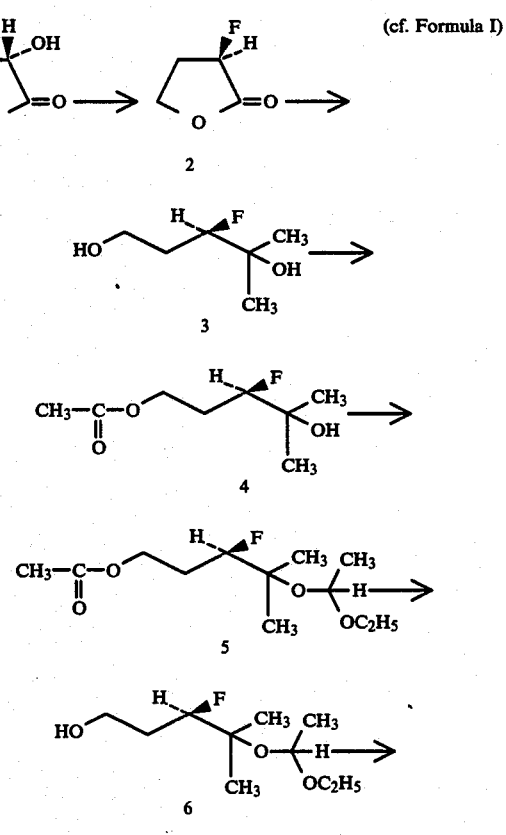

-continued

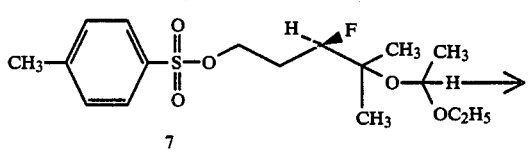
7

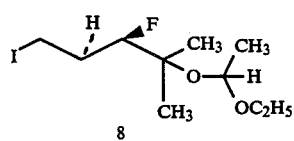
8

The (−)-2S-hydroxy-4-butyrolactone (1) was treated with diethylaminosulfur trifluoride in methylene chloride at −78° C. to yield the 2R-fluoro-4-butyrolactone 2 which was treated with methyllithium in ether to give diol 3. Diol 3 was selectively acetylated with acetic anhydride and pyridine to yield 4. This substance was treated with ethyl vinyl ether and a catalytic amount of p-toluenesulfonic acid to give 5. Alternatively, compound 4 could be reacted with vinyl ethers such as lower alkyl vinyl ethers, phenyl vinyl ethers, substituted phenyl vinyl ethers and cyclic vinyl ethers. Exemplary of lower alkyl vinyl ethers are methyl vinyl ether, ethyl vinyl ether, methyl 1-methylvinyl ether, methyl 2-methylvinyl ether and the like. Exemplary of phenyl vinyl ethers are phenyl vinyl ether, phenyl 1-methylvinyl ether, phenyl 2-methylvinyl ether and the like. Exemplary of substituted phenyl vinyl ethers are 4-methylphenyl vinyl ether, 4-chlorophenyl vinyl ether, 4-methylphenyl 1-methylvinyl ether and the like. Exemplary of cyclic vinyl ethers are 3,4-dihydro-2H-pyrans and 2,3-dihydro-2H-furans.

Compound 5 and the like may be treated with metal aluminum hydride reducing agents such as lithium aluminum hydride to yield compound 6 and the like. Compound 6 and the like may be treated with a proper sulfonyl halide such as lower alkyl sulfonyl halides, phenyl sulfonyl halides, substituted phenyl sulfonyl halides and the like to yield compound 7 and the like. Examples are methanesulfonyl chloride, benzenesulfonyl bromide and p-toluenesulfonyl chloride. Compound 7 and the like may be treated with alkali metal halides to yield compound 8 and the like. Examples of alkali metal halides are sodium iodide, sodium bromide, potassium iodide, potassium bromide and the like.

Compounds 7 and 8 correspond to the compound of formula I with the R-absolute configuration at the carbon bearing fluoride. In the same manner, (+)-2R-hydroxy-4-butyrolactone [J. W. E. Glattfield and F. V. Sander, J. Amer. Chem. Soc., 43, 2675 (1921)] was converted to compounds of formula I with the S-absolute configuration at the carbon bearing fluorine. Also in the same manner (±)-2-hydroxy-4-butyrolactone was converted to compounds of formula I with the racemic or 1:1 R,S-absolute configuration at the carbon bearing fluorine.

The preparation of a compound of formula IV is shown in the scheme below beginning with the known 1α,3β-dihydroxyandrost-5-en-17-one [R. M. Dodson, A. H. Goldkamp and R. D. Muir, J. Amer. Chem. Soc., 82, 4026 (1960)].

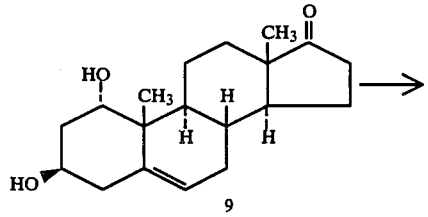
9

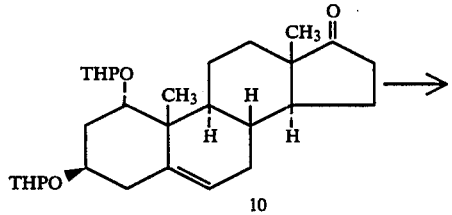
10

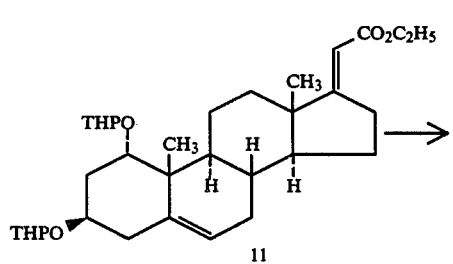
11

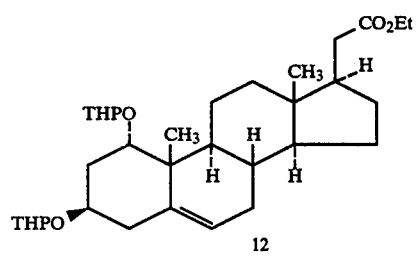
12

The 1α,3β-dihydroxyandrost-5-en-17-one (9) was stirred with 3,4-dihydro-2H-pyran and p-toluenesulfonic acid to yield ketone 10. This substance was treated with triethylphosphonoacetate and ethanolic sodium ethoxide to yield the unsaturated ester 11. Catalytic hydrogenation of 11 over platinum oxide catalyst then afforded [1α,3β]-1,3-bis[(tetrahydro-2H-pyran-2-yl)oxy]pregn-5-en-21-oic acid ethyl ester (12), which corresponds to compounds of the formula IV. The sequence (9→12) parallels the work of J. Wicha and K. Bal, J. Chem. Soc. Perkin Trans. I, 1282 (1978).

1α,25-Dihydroxy-24R-fluorocholecalciferol has shown activity in the antirachitogenic test in chicks and has also shown a duration of activity in stimulation of intestinal calcium absorption of 24 hours after a single oral 100 nanogram dose, comparable to that of 1α,25-dihydroxycholecalciferol.

(a) Anti-Rachitogenic Activity in Chicks

One-day-old White Leghorn cockerels are placed on a vitamin D-deficient diet which contains 1% calcium and 0.7% phosphorus and are housed under ultraviolet-free lighting (General Electric F40G40 gold fluorescent lights). Compounds are dissolved in propylene glycol and administered orally in a volume of 0.2 ml for 21 consecutive days to chicks which are one to two days of age at the start of treatment. Controls are treated with vehicle alone. Compounds are prepared in amber flasks and the solutions are flushed with argon and refrigerated after each dosing period. Chicks are autopsied on the day after the last treatment day. Blood is collected for determination of serum calcium and phosphorus and tibia dry weight and ash weight are determined. Usually, ten chicks are used for each treatment group and for the control group. The results of the 1α,25-dihydroxy-24R-fluorocholecalciferol anti-rachitogenic activity assay are shown in Table I along with comparative data showing the anti-rachitogenic activity of 24,24-difluoro 1α,25-dihydroxycholecalciferol. The results show that 1α,25-dihydroxy-24R-fluorocholecalciferol possesses potent anti-rachitogenic activity.

TABLE I

ANTI-RACHITOGENIC ACTIVITIES OF
24,24-DIFLUORO-1α,25-DIHYDROXYCHOLECALCIFEROL
AND 1α,25-DIHYDROXY-24 R-FLUOROCHOLE-
CALCIFEROL IN CHICKS

A = 24,24-DIFLUORO-1α,25-DIHYDROXYCHOLECALCIFEROL
B = 1α,25-DIHYDROXY-24 R-FLUOROCHOLECALICIFEROL

| DOSE NG/CHICK/DAY | MEAN TIBIA ASH WEIGHT (MG) + S.E. | |
|---|---|---|
|  | A | B |
| 0 | 120.9 ± 8.3 | |
| 3 | 192.2 ± 6.2*** | 293.3 ± 4.8*** |
| 10 | 258.6 ± 10.0*** | 330.4 ± 7.7*** |
| 30 | 229.8 ± 14.2*** | 337.9 ± 10.6*** |

21 DAYS ORAL DOSING
9–10 CHICKS PER GROUP
***STATISTICALLY SIGNIFICANT RESULT (b) Intestinal Calcium Absorption in Chicks White Leghorn one-day-old cockerels are placed on a vitamin D-deficient diet and are housed under ultraviolet-free lighting for 21 days. Chicks are then used to determine the effects of test compounds on intestinal calcium absorption. A single oral dose of test compound dissolved in propylene glycol is administered. At various times after dosing, 2 uCi of $^{45}$Ca (chloride) is given orally, and serum radioactivity is measured 45 minutes after administration of the isotope. Ten chicks are used in each treatment and control group and vehicle-treated controls are included at each time period. The results of the intestinal calcium absorption assay are shown in Table II. The results show that 1α,25-dihydroxy-24R-fluorocholecalciferol has intestinal calcium absorption activity of about 24 hours duration.

TABLE II

EFFECT OF 1α,25-DIHYDROXY-24
R-FLUOROCHOLECALCIFEROL $^{45}$CA
ABSORPTION IN VITAMIN D-DEFICIENT CHICKS

A = 1α,25-DIHYDROXY-24 R-FLUOROCHOLECALCIFEROL

| TREATMENT (ORAL) | TIME (HR) | NO. OF CHICKS | SERUM $^{45}$CA CPM/0.2 ML |
|---|---|---|---|
| VEHICLE, 0.2 ML | 24 | 10 | 408 ± 30 |
| A |  | 10 | 793 ± 73*** |
| VEHICLE, 0.2 ML | 48 | 10 | 439 ± 30 |
| A |  | 10 | 520 ± 38NS |
| VEHICLE, 0.2 ML | 72 | 10 | 398 ± 31 |
| A |  | 10 | 372 ± 39 NS |

***STATISTICALLY SIGNIFICANT RESULT
NS = NOT STATISTICALLY SIGNIFICANT

1α,25-Dihydroxy-24R-fluorocholecalciferol can be administered in dosages that are in the range of about 0.10–3.0 micrograms/per day for the treatment of such disease states as osteodystrophy, steroid induced osteopenia, hypoparathyroidism, hypophosphatemic rickets and hypophosphatemic osteomalacia which are characterized by lower than normal levels of endogenously produced 1α,25-dihydroxycholecalciferol. Preferable dosage ranges are 0.25–2.0 micrograms per day for the treatment of the aforementioned disease states. 1α,25-Dihydroxy-24R-fluorocholecalciferol can be administered orally, subcutaneously, intramuscularly, intravenously, intraperitoneally or topically.

1α,25-dihydroxy-24R-fluorocholecalciferol can be formulated into compositions such as tablets, capsules, and the like, or elixers for oral administration, or in sterile solutions or suspensions for parenteral administration for the treatment of the aforementioned disease states. About 0.10–3.0 micrograms, preferably 0.25–2.0 micrograms, is compounded with a pharmaceutically acceptable vehicle, carrier, excipient, binder, preservative, stabilizer, flavor, and the like, in a unit dosage as called for by accepted pharmaceutical practice. The amount of active substance in the foregoing compositions or preparations is in the range previously indicated.

Illustrative of the adjuvants which may be incorporated into capsules, and the ike are the following: a binder such as gum tragacanth, acacia, corn starch, or gelatin; an excipient such as calcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen, or cherry. Various other materials may be present as coatings or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

1α,25-Dihydroxy-24R-fluorocholecalciferol can be administered for the treatment of milk fever in pregnant ruminant animals prior to parturation in dosages in th range of 100–1500 micrograms/day using conventional formulations.

Sterile compositions for injection and/or topical administration can be formulated according to conventional practice by dissolving or suspending 1α,25-dihydroxy-24R-fluorocholecalciferol in a vehicle such as a 10–20% ethanol-water mixture, a 10–20% propylene glycol-water mixture a naturally-occurring vegetable oil, such as sesame oil, peanut oil, cottonseed oil, and the like, or a synthetic fatty vehicle such as ethyl oleate or the like. For example, a suitable formulation for intravenous injection would be 2–3 ml of a 10–20% ethanol-water solution or a 10–20% propylene glycol-water mixture containing 100–1500 micrograms of 1α,25-dihydroxy-fluorocholecalciferol. Such a formulation would preferably contain 200–1000 micrograms of 1α,25-dihydroxy-24R-fluorocholecalciferol. Exemplary of a suitable formulation for topical administration would be a vegetable oil solution or suspension containing 100–1500 micrograms of 1α,25-dihydroxy-24R-fluorocholecalciferol. Such a formulation would preferably contain 200–1000 micrograms of 1α,25-dihydroxy-24R-fluorocholecalciferol.

1α,25-dihydroxy-24R-fluorocholecalciferol can also be formulated for oral administration by incorporation of 100–1500 micrograms of 1α,25-dihydroxy-24R-fluorocholecalciferol into fatty acid pellets.

1α,25-dihydroxy-24R-fluorocholecalciferol may also be formulated for intramuscular injection by suspension of 100-1500 micrograms of 1α,25-dihydroxy-24R-fluorocholecalciferol in a vehicle such as a vegetable oil, an ethanol-water solution containing from 80-95% ethanol or a propylene glycol-water solution containing from 80-95% propylene glycol.

Buffers, preservatives, antioxidants and the like can be incorporated into the foregoing formulations as required.

EXAMPLE 1

To a solution of 16.5 g. (0.102 mole) of diethylaminosulfur trifluoride (DAST) in 20 ml. of methylene chloride at −70° C. was added dropwise 3.50 g (0.034 mole) of (−)-2S-hydroxy-4-butyrolactone [J. W. E. Glattfeld and F. V. Sander, *J. Amer. Chem. Soc.*, 43, 2675 (1921)] in 30 ml. of methylene chloride. The mixture was stirred at −70° C. for 1 hr and was warmed to 25° C. and stirred 1 hr. The mixture was slowly poured into saturated aqueous sodium bicarbonate solution at 0° C. The product was extracted with methylene chloride. The organic phase was dried over anhydrous magnesium sulfate, filtered, and evaporated to dryness. The residue was purified by column chromatography on 200 g. of silica gel (0.06–0.20 mm) to yield 2R-fluoro-4-butyrolactone, $[\alpha]_D^{22}+50°$ (c 1, CHCl$_3$).

EXAMPLE 2

To a solution of 8.25 g. (0.051 mole) of diethylaminosulfur trifluoride (DAST) in 15 ml. of methylene chloride at −70° C. was added dropwise 1.75 g. (0.017 mole) of (+)-2R-hydroxy-4-butyrolactone [J. W. E. Glattfeld and F. V. Sander, *J. Amer. Chem. Soc.*, 43, 2675 (1921)] in 15 ml. of methylene chloride. The mixture was stirred at −70° C. for 1 hr and was warmed to 25° C. and stirred for 1 hr. The mixture was slowly poured into saturated aqueous sodium bicarbonate solution at 0° C. The product was extracted with methylene chloride. The organic phase was dried over anhydrous magnesium sulfate, filtered, and evaporated to dryness. The residue was purified by column chromatography on 75 g. of silica gel (0.06–0.20 mm) to yield 2S-fluoro-4-butyrolactone, $[\alpha]^{23}-51°$ (c 0.9, CHCl$_3$).

EXAMPLE 3

To a solution of 16.8 ml. of 1.5M ethereal methyllithium (0.025 mole) at 0° was added dropwise 1.05 g. (0.010 mole) of 2R-fluoro-4-butyrolactone in 35 ml. of ether. The mixture was stirred at 0° C. for 1 hr and at 25° C. for 1 hr. The mixture was quenched by adding 2 ml. of saturated brine at 0° C. The mixture was poured into saturated brine and the product was isolated with ether. The ether layers were dried over anhydrous magnesium sulfate, filtered, and evaporated to dryness to give 4-methyl-3R-fluoro-1,4-pentanediol, $[\alpha]_D^{22}+39°$ (c 1, CHCl$_3$).

EXAMPLE 4

To a solution of 16.8 ml. of 1.5M ethereal methyllithium (0.025 mole) at 0° was added dropwise 1.04 g. (0.010 mole) of 2S-fluoro-4-butyrolactone in 30 ml. of ether. The mixture was stirred at 0° C. for 1 hr and at 25° C. for 1 hr. The mixture was quenched by the dropwise addition of 2 ml. of saturated brine. The mixture was poured into saturated brine and the product was isolated with ether. The ether layers were dried over anhydrous magnesium sulfate, filtered, and evaporated to dryness to yield 4-methyl-3S-fluoro-1,4-pentanediol, $[\alpha]_D^{22}-40°$ (c 1, CHCl$_3$).

EXAMPLE 5

To a mixture of 0.540 g. (0.0040 mole) of 4-methyl-3R-fluoro-1,4-pentanediol and 3 ml. of pyridine at 0° C. was added 2 ml. of acetic anhydride and the mixture was stirred at 0° C. for 1 hr and at 25° C. for 1 hr. The mixture was added to 10 ml. of methanol and the solution was evaporated to dryness to yield oily 4-methyl-3R-fluoro-1,4-pentanediol 1-acetate, $[\alpha]_D^{22}+49°$ (c 0.5, CHCl$_3$).

EXAMPLE 6

To a mixture of 0.27 g. (0.0020 mole) of 4-methyl-3S-fluoro-1,4-pentanediol and 2 ml. of pyridine at 0° C. was added 1 ml. of acetic anhydride and the mixture was stirred at 0° C. for 1 hr and at 25° C. for 1 hr. The mixture was added to 5 ml. of methanol and the solution was evaporated to dryness to yield oily 4-methyl-3S-fluoro-1,4-pentanediol 1-acetate, $[\alpha]_D^{22}-49°$ (c 0.5, CHCl$_3$).

EXAMPLE 7

A mixture of 2.48 g (0.014 mole) of 4-methyl-3R-fluoro-1,4-pentanediol 1-acetate, 65 ml of ethyl vinyl ether and 0.25 g. of p-toluenesulfonic acid monohydrate were stirred at −70° C. for 1 hr. The mixture was quenched by adding 8 ml. of triethylamine and evaporated to dryness. The residue was taken up in ether. This solution was successively washed with saturated aqueous sodium bicarbonate solution and saturated brine. The ether phase was dried over anhydrous magnesium sulfate, filtered and evaporated to dryness to yield an oil containing 4-(1-ethoxyethoxy)-3R-fluoro-4-methyl-1-pentanol 1-acetate.

EXAMPLE 8

A mixture of 0.60 g (0.0034 mole) of 4-methyl-3S-fluoro-1,4-pentanediol 1-acetate, 12 ml. of ethyl vinyl ether and 0.06 g. of p-toluenesulfonic acid monohydrate was stirred at −70° C. for 1 hr. The mixture was then quenched with 2 ml. of triethylamine and evaporated to dryness. The residue was taken up in ether. This solution was successively washed with saturated aqueous sodium bicarbonate solution and saturated brine. The ether phase was dried over anhydrous magnesium sulfate, filtered, and evaporated to dryness to yield an oil containing 4-(1-ethoxyethoxy)-3S-fluoro-4-methyl-1-pentanol 1acetate.

EXAMPLE 9

To a mixture of 0.79 g. (0.021 mole) of lithium aluminum hydride in 40 ml. of ether at 0° C. was added dropwise, 3.48 g. (0.014 mole) of 4-(1-ethoxyethoxy)-3R-fluoro-4-methyl-1-pentanol 1-acetate in 100 ml. of ether. The mixture was heated at reflux (35° C.) for 3 hr. and then was recooled to 0° C. The mixture was quenched by adding dropwise 1.5 ml. of water followed by 1.2 ml. of 10% aqueous sodium hydroxide. The mixture was stirred at 25° C. for 0.5 hr and was filtered. The solids were triturated with ether and filtered. Evaporation of solvent and column chromatography of the residue on 0.06–0.20 mm silica gel afforded 4-(1-ethoxyethoxy)-3R-fluoro-4-methyl-1-pentanol, $[\alpha]_D^{24}+18°$ (c 1, CHCl$_3$).

EXAMPLE 10

To a mixture of 0.07 g. (0.0018 mole) of lithium aluminum hydride in 3 ml. of ether at 0° C. was added dropwise 0.077 g. (0.00031 mole) of 4-(1-ethoxyethoxy)-3S-fluoro-4-methyl-1-pentanol 1-acetate in 7 ml. of ether. The mixture was heated at reflux (35° C.) for 3 hr and then was recooled to 0° C. The mixture was quenched by adding dropwise 0.14 ml. of water followed by 0.11 ml. of 10% aqueous sodium hydroxide. The mixture was stirred at 25° C. for 0.5 hr and was filtered. The solids were triturated with ether and filtered. Evaporation of solvent and column chromatography of the residue on 0.06–0.20 mm silica gel afforded 4-(1-ethoxyethoxy)-3S-fluoro-4-methyl-1-pentanol, $[\alpha]_D^{22}-16°$ (c 1, CHCl$_3$).

EXAMPLE 11

A mixture of 3.34 g. (0.016 mole) of 4-(1-ethoxyethoxy)-3R-fluoro-4-methyl-1-pentanol, 12 ml. of pyridine and 4.67 g. (0.024 mole) of p-toluenesulfonyl chloride was stirred at 0° C. for 18 hr. The mixture was quenched with ice chips. The mixture was then poured into water and extracted with methylene chloride. The organic phase was sequentially washed with 10% aqueous sulfuric acid and saturated aqueous sodium bicarbonate solution. The organic phase was dried over anhydrous magnesium sulfate, filtered and evaporated to dryness to yield oily 4-(1-ethoxyethoxy)-3R-fluoro-4-methyl-1-pentanol 1-(4-methylbenzenesulfonate).

EXAMPLE 12

A mixture of 0.21 g. (0.0010 mole) of 4-(1-ethoxyethoxy)-3S-fluoro-4-methyl-1-pentanol, 1 ml. of pyridine and 0.28 g. (0.0015 mole) of p-toluenesulfonyl chloride was stirred at 0° C. for 18 hr. The mixture was quenched with a chip of ice. The mixture was then poured into water and extracted with methylene chloride. The organic phase was sequentially washed with 10% aqueous sulfuric acid and saturated aqueous sodium bicarbonate solution. The organic phase was dried over anhydrous magnesium sulfate, filtered, and evaporated to dryness to yield oily 4-(1-ethoxyethoxy)-3S-fluoro-4-methyl-1-pentanol 1-(4-methylbenzenesulfonate).

EXAMPLE 13

A mixture of 5.42 g. (0.015 mole) of 4-(1-ethoxyethoxy)-3R-fluoro-4-methyl-1-pentanol 1-(4-methylbenzenesulfonate), 70 ml. of acetone, 1 ml. of diisopropylethylamine and 30.3 g. (0.202 mole) of sodium iodide was stirred at 25° C. for 18 hr. The mixture was evaporated to dryness. The residue was partitioned between 5% aqueous sodium sulfite solution and methylene chloride. The organic phase was washed with saturated aqueous sodium bicarbonate solution. The organic phase was then dried over anhydrous magnesium sulfate, filtered, and evaporated to dryness to yield 4-(1-ethoxyethoxy)-3R-fluoro-1-iodo-4-methylpentane, $[\alpha]_D^{24}+43°$ (c 1, CHCl$_3$).

EXAMPLE 14

A mixture of 0.36 g. (0.0010 mole) of 4-(1-ethoxyethoxy)-3S-fluoro-4-methyl-1-pentanol 1-(4-methylbenzenesulfonate), 5 ml. of acetone, 0.10 ml. of diisopropylethylamine, and 1.94 g. (0.013 mole) of sodium iodide was stirred at 25° C. for 18 hr. The mixture was evaporated to dryness. The residue was partitioned between 5% aqueous sodium sulfite and methylene chloride. The organic phase was washed with saturated aqueous sodium bicarbonate solution. The organic phase was then dried over anhydrous magnesium sulfate, filtered and evaporated to dryness to yield 4-(1-ethoxyethoxy)-3S-fluoro-1-iodo-4-methylpentane, $[\alpha]_D^{22}-38°$ (c 1, CHCl$_3$).

EXAMPLE 15

A mixture of 0.91 g. (0.0030 mole) of 1α,3β-dihydroxyandrost-5-en-17-one [R. M. Dodson, A. H. Goldkamp and R. D. Muir, *J.Amer. Chem.Soc.*, 82, 4026 (1960)], 15 ml. of tetrahydrofuran, 1.26 g. (0.015 mole) of 3,4-dihydro-2H-pyran and 0.028 mg. of p-toluenesulfonic acid monohydrate was stirred at 25° for 18 hr. The mixture was diluted with methylene chloride. This solution was then washed with saturated aqueous sodium bicarbonate solution. The organic phase was dried over anhydrous magnesium sulfate, filtered and evaporated to dryness to yield oily [1α,3β]-1,3-bis[(tetrahydro-2H-pyran-2-yl)oxy]androst-3-en-17-one, $[\alpha]_D^{20}+34.3°$ (c 1, CHCl$_3$).

EXAMPLE 16

To a mixture of 1.00 g. (0.0021 mole) of [1α,3β]-1,3-bis[(tetrahydro-2H-pyran-2-yl)oxy]androst-3-en-17-one, 1.94 g. (0.0087 mole) of triethyl phosphonoacetate, and 14 ml. of ethyl alcohol was added 0.68 g. (0.010 mole) of sodium ethoxide in 7 ml. of ethanol. The mixture was stirred at reflux (80° C.) for 18 hr. and cooled. The mixture was concentrated under reduced pressure. The residue was partitioned between water and ether and the organic phase was washed with saturated brine. The organic phase was then dried over anhydrous magnesium sulfate, filtered, and evaporated to dryness. The residue was chromatographed on 0.06–0.20 mm silica gel to yield [1α,3β,17(20)E]-1,3-bis[(tetra-2H-pyran-2-yl)oxy]pregna-5,17(20)-dien-21-oic acid ethyl ester, $[\alpha]_D^{20}-8°$ (c 1, CHCl$_3$).

EXAMPLE 17

A mixture of 0.32 g. (0.00059 mole) of [1α,3β,17(-20)E]-1,3-bis[(tetrahydro-2H-pyran-2-yl)oxy]pregna-5,17(20)-dien-21-oic acid ethyl ester, 0.10 g. of platinum oxide, and 20 ml. of ethanol was stirred in 1 atmosphere of hydrogen for 2 hr. The mixture was filtered through a pad of diatomaceous earth and the solids were washed with ethanol. The combined filtrates were evaporated to dryness to yield oily [1α,3β]-1,3-bis[(tetrahydro-2H-pyran-2-yl)oxy]pregn-5-en-21-oic acid ethyl ester, $[\alpha]_D^{23}-13°$ (c 1, CHCl$_3$).

EXAMPLE 18

To a solution of 1.2 ml. of diisopropylamine in 4 ml. of tetrahydrofuran at −30° C. was added 4.5 ml. (0.0072 mole) of 1.6M of butyllithium in hexane. After stirring for 0.5 hr, 3.57 g (0.0065 mole) of [1α,3β]-1,3-bis[(tetrahydro-2H-pyran-2-yl)oxy]pregn-5-en-21-oic acid ethyl ester in 36 ml. of tetrahydrofuran was added dropwise. The mixture was stirred for 1 hr at −30° C. and cooled to −70° C. A solution of 3.40 g. (0.011 mole) of 4-(1-ethoxyethoxy)-3R-fluoro-1-iodo-4-methylpentane in 6 ml. of hexamethylphosphoramide was added dropwise. The mixture was stirred at −70° C. for 1 hr and was allowed to warm to 25° C. and stir for 1 hr. The mixture was then diluted with 9:1 hexane-ether. The solution was washed with water, and saturated brine. The organic phase was dried over anhydrous magnesium sulfate, filtered, and evaporated to dryness. The residue was purified by column chromatography on 0.06–0.20 mm silica gel to give [1α,3β,24R]-1,3-bis[(tetrahydro-2H-pyran-2-yl)oxy]-25-(1-ethoxyethoxy)-24-fluorocholest-5-en-21-oic acid ethyl ester, $[\alpha]_D^{20}+18°$ (c 1, CHCl$_3$).

EXAMPLE 19

To a solution of 0.24 ml. of diisopropylamine in 1 ml. of tetrahydrofuran at −30° was added 0.88 ml. of 1.6M butyllithium in hexane. After stirring for 0.5 hr, 0.70 g. (0.0013 mole) of [1α,3β]-1,3-bis[(tetrahydro-2H-pyran-2-yl)oxy]pregn-5-en-21-oic acid ethyl ester in 7 ml. of tetrahydrofuran was added dropwise. The mixture was stirred for 1 hr at −30° C. and cooled to −70° C. A solution of 0.50 g. (0.0016 mole) of 4-(1-ethoxyethoxy)-3S-fluoro-1-iodo-4-methylpentane in 1 ml. of hexamethylphosphoramide was then added dropwise. The mixture was stirred at −70° C. for 1 hr and was allowed to warm to 25° C. and stir for 1 hr. The mixture was diluted with 9:1 hexane-ether. The solution was washed with water, and saturated brine. The organic phase was dried over anhydrous magnesium sulfate, filtered, and evaporated to dryness. The residue was purified by column chromatography on 0.06–0.20 mm silica gel to give [1α,3β,24S]-1,3-bis[(tetrahydro-2H-pyran-2-yl)oxy]-25-(1-ethoxyethoxy)-24-fluorocholest-5-en-21-oic acid ethyl ester.

EXAMPLE 20

To a mixture of 0.34 g. (0.0090 mole) of lithium aluminum hydride and 17 ml. of tetrahydrofuran at 0° C. was added 4.26 g. of [1α,3β,24R]-1,3-bis[(tetrahydro-2H-pyran-2-yl)oxy]-25-(1-ethoxyethoxy)-24-fluorocholest-5-en-21-oic acid ethyl ester in 60 ml. of tetrahydrofuran. The mixture was heated at 50° C. for 1.5 hr, recooled to 0° C., and diluted with 200 ml. of ether. The mixture was then quenched with the dropwise addition of 0.68 ml. of water and 0.55 ml. of 10% aqueous sodium hydroxide. The mixture was stirred at 25° C. for 0.5 hr and was filtered. The solids were triturated with ether and filtered. Evaporation of solvent afforded [1α,3β,24R]-1,3-bis[(tetrahydro-2H-pyran-2-yl)oxy]-25-(1-ethoxyethoxy)-24-fluorocholest-5-en-21-ol, $[\alpha]_D^{25}+7°$ (c 1.1, CHCl$_3$).

EXAMPLE 21

To a mixture of 0.028 g. (0.00074 mole) of lithium aluminum hydride in 1 ml. of tetrahydrofuran at 0° C. was added 0.200 g. (0.00027 mole) of [1α,3β,24S]-1,3-bis[(tetrahydro-2H-pyran-2-yl)oxy]-25-(1-ethoxyethoxy)-24-fluorocholest-5-en-21-oic acid ethyl ester in 3 ml. of tetrahydrofuran. The mixture was stirred at 50° C. for 1.5 hr, recooled to 0° C. and diluted with 12 ml. of ether. The mixture was then quenched with the dropwise addition of 0.06 ml. of water and 0.05 ml. of 10% aqueous sodium hydroxide. The mixture was stirred at 25° C. for 0.5 hr and was filtered. The solids were triturated with ether and filtered. Evaporation of solvent afforded [1α,3β,24S]-1,3-bis[(tetrahydro-2H-pyran-2-yl)oxy]-25-(1-ethoxyethoxy)-24-fluorocholest-5-en-21-ol.

EXAMPLE 22

A mixture of 3.99 g. (0.0058 mole) of [1α,3β,24R]-1,3-bis[(tetrahydro-2H-pyran-2-yl)oxy]-25-(1-ethoxyethoxy)-24-fluorocholest-5-en-21-ol, 15 ml. of pyridine and 2.20 g. (0.0115 mole) of p-toluenesulfonyl chloride was stirred at 0° C. for 18 hr. The mixture was quenched with ice chips. The mixture was then poured into water and extracted with methylene chloride. The organic phase was washed with 10% aqueous sulfuric acid and saturated aqueous sodium bicarbonate solution. The organic layer was dried over anhydrous magnesium sulfate, filtered and evaporated to dryness to yield oily [1α,3β,24R]-1,3-bis[(tetrahydro-2H-pyran-2-yl)oxy]-25-(1-ethoxyethoxy)-24-fluorocholest-5-en-21-ol 21-(4-methylbenzenesulfonate), $[\alpha]_D^{20}+8°$ (c 1, CHCl$_3$).

EXAMPLE 23

A mixture of 0.19 g. (0.00027 mole) of [1α,3β,24S]-1,3-bis[(tetrahydro-2H-pyran-2-yl)oxy]-25-(1-ethoxyethoxy)-24-fluorocholest-5-en-21-ol, 1 ml. of pyridine and 0.104 g. (0.00054 mole) of p-toluenesulfonyl chloride was stirred at 0° C. for 18 hr. The mixture was quenched with ice chips. The mixture was then poured into water and extracted with methylene chloride. The organic phase was washed with 10% aqueous sulfuric acid and saturated aqueous sodium bicarbonate solution. The organic layer was dried over anhydrous magnesium sulfate, filtered, and evaporated to dryness to yield oily [1α,3β,24S]-1,3-bis[(tetrahydro-2H-pyran-2-yl)oxy]-25-(1-ethoxyethoxy)-24-fluorocholest-5-en-21-ol 21-(4-methylbenzenesulfonate).

EXAMPLE 24

A mixture of 0.223 g. (0.00026 mole) of [1α,3β,24R]-1,3-bis[(tetrahydro-2H-pyran-2-yl)oxy]-25-(1-ethoxyethoxy)-24-fluorocholest-5-en-21-ol 21-(4-methylbenzenesulfonate), and 0.150 g. (0.0010 mole) of sodium iodide in 2 ml. of acetone was heated at 50° for 18 hr and cooled. The mixture was poured into water and the product was isolated with methylene chloride. The organic layers were washed with aqueous sodium sulfite solution, and saturated aqueous sodium bicarbonate solution. The organic layers were dried over anhydrous magnesium sulfate, filtered and evaporated to dryness to yield [1α,3β,24R]-1,3-bis[(tetrahydro-2H-pyran-2-yl)oxy]-25-(1-ethoxyethoxy)-24-fluoro-21-iodocholest-5-ene.

EXAMPLE 25

A mixture of 0.220 g. (0.00026 mole) of [1α,3β,24S]-1,3-bis[(tetrahydro-2H-pyran-2-yl)oxy]-25-(1-ethoxyethoxy)-24-fluorocholest-5-en-21-ol 21-(4-methylbenzenesulfonate), and 0.165 g. (0.0011 mole) of sodium iodide in 2 ml of acetone was heated at 50° for 18 hr and cooled. The mixture was poured into water and the product was isolated with methylene chloride. The organic layers were washed with aqueous sodium sulfite solution, and saturated aqueous sodium bicarbonate solution. The organic layers were dried over anhydrous magnesium sulfate, filtered and evaporated to dryness to yield [1α,3β,24S]-1,3-bis[(tetrahydro-2H-pyran-2-yl)oxy]-25-(1-ethoxyethoxy)-24-fluoro-21-iodocholest-5-ene.

EXAMPLE 26

A. A mixture of 0.710 g. (0.0187 mole) of lithium aluminum hydride, 80 ml. of tetrahydrofuran and 4.85 g. (0.0057 mole) of [1α,3β,24R]-1,3-bis[(tetrahydro-2H-pyran-2-yl)oxy]-25-(1-ethoxyethoxy)-24-fluorocholest-5-en-21-ol 21-(4-methylbenzenesulfonate) was heated at reflux (60° C.) for 1 hr and cooled to 0° C. The mixture was diluted with 200 ml. of ether and quenched with the dropwise addition of 1.4 ml. of water and 1.1 ml. of 10% aqueous sodium hydroxide solution. The mixture was then stirred for 1 hr and filtered. The solids were triturated with ether and filtered. The combined filtrates were evaporated to dryness and chromatographed on 0.06–0.20 mm silica gel to yield [1α,3β,24R]-1,3-bis[(tetrahydro-2H-pyran-2-yl)oxy]-25-(1-ethoxyethoxy)-24-fluorocholest-5-ene, $[\alpha]_D^{20}+7°$ (c 1, CHCl$_3$).

B. By an alternative procedure, a mixture of 0.206 g. (0.00025 mole) of [1α,3β,24R]-1,3-bis[(tetrahydro-2H-pyran-2-yl)oxy]-25-(1-ethoxyethoxy)-24-fluoro-21-iodocholest-5-ene, 0.087 g. (0.00030 mole) of tri-n-butyltin hydride and 3 ml of tetrahydrofuran were stirred at 25° C. for 18 hr under an argon atmosphere. The mixture was evaporated to dryness and the residue was purified by chromatography on 0.06–0.20 mm silica gel to yield [1α,3β,24R]-1,3-bis[(tetrahydro-2H-pyran-2-yl)oxy]-25-(1-ethoxyethoxy)-24-fluorocholest-5-ene, $[\alpha]_D^{21}+7°$ (c 1, CHCl$_3$).

EXAMPLE 27

A. A mixture of 0.033 g. (0.00088 mole) of lithium aluminum hydride, 4 ml. of tetrahydrofuran, and 0.223 g. (0.00026 mole) of [1α,3β,24S]-1,3-bis[(tetrahydro-2H-pyran-2-yl)oxy]-25-(1-ethoxyethoxy)-24-fluorocholest-5-en-21-ol 21-(4-methylbenzenesulfonate) was heated at reflux (60° C.) for 1 hr and cooled to 0° C. The mixture was diluted with 12 ml. of ether and quenched with the dropwise addition of 0.07 ml. of water and 0.05 ml. of 10% aqueous sodium hydroxide solution. The mixture was then stirred for 1 hr and filtered. The solids were triturated with ether and filtered. The combined filtrates were evaporated to dryness and chromatographed on 0.06–0.20 mm silica gel to yield [1α,3β,24S]-1,3-bis[(tetrahydro-2H-pyran-2-yl)oxy]-25-(1-ethoxyethoxy)-24-fluorocholest-5-ene.

B. By an alternative proceudre, a mixture of 0.208 g. (0.00025 mole) of [1α,3β,24S]-1,3-bis[(tetrahydro-2H-pyran-2-yl)oxy]-25-(1-ethoxyethoxy)-24-fluoro-21-iodocholest-5-ene, 0.087 g. (0.00030 mole) of tri-n-butyltin hydride and 3 ml of tetrahydrofuran were stirred at 25° C. for 18 hr under an argon atmosphere. The mixture was evaporated to dryness and the residue was purified by chromatography on 0.06–0.20 mm silica gel to yield [1α,3β,24S]-1,3-bis[(tetrahydro-2H-pyran-2-yl)oxy]-25-(1-ethoxyethoxy)-24-fluorocholest-5-ene.

EXAMPLE 28

A mixture of 3.56 g. (0.0053 mole) of [1α,3β,24R]-1,3-bis[(tetrahydro-2H-pyran-2-yl)oxy]-25-(1-ethoxyethoxy)-24-fluorocholest-5-ene, 140 ml. of methanol and 0.58 g. of p-toluenesulfonic acid monohydrate was stirred at 25° C. for 3 hr. The mixture was quenched by adding 1.0 g. of sodium bicarbonate and stirring for 0.5 hr. The mixture was then evaporated to dryness. The residue was triturated with ethyl acetate, filtered, and evaporated to dryness. The crude solid was recrystallized from ethyl acetate to yield [1α,3β,24R]-24-fluorocholest-5-en-1,3,25-triol, mp 156°–158°, $[\alpha]_D^{21}+4°$ (c 0.5, MeOH).

EXAMPLE 29

A mixture of 0.356 g. (0.00053 mole) of [1α,3β,24S]-1,3-bis[(tetrahydro-2H-pyran-2-yl)oxy]-25-(1-ethoxyethoxy)-24-fluorocholest-5-ene, 15 ml. of methanol and 0.05 g. of p-toluenesulfonic acid monohydrate was stirred at 25° for 3 hr. The mixture was quenched with 0.25 g. of sodium bicarbonate and stirring for 0.5 hr. The mixture was evaporated to dryness. The residue was triturated with ethyl acetate, filtered, and evaporated to dryness to yield [1α,3β,24S]-24-fluorocholest-5-en-1,3,25-triol.

EXAMPLE 30

A mixture of 1.53 g. (0.0035 mole) of [1α,3β,24R]-24-fluorocholest-5-en-1,3,25-triol, 13 ml. of pyridine and 6 ml. of acetic anhydride were stirred at 0° C. for 1 hr and at 25° for 17 hr. The mixture was diluted with 20 ml. of methanol at 0° C. and evaporated to dryness. The residue was then dissolved in methylene chloride. This solution was washed with 10% aqueous sulfuric acid and saturated sodium bicarbonate solution. The organic phase was dried over anhydrous magnesium sulfate, filtered, and evaporated to dryness to yield [1α,3β,24R]-24-fluorocholest-5-en-1,3,25-triol, 1,3-diacetate, $[\alpha]_D^{23}-7°$ (c 1, CHCl$_3$).

EXAMPLE 31

A mixture of 0.436 g. (0.0010 mole) of [1α,3β,24S]-24-fluorocholest-5-en-1,3,25-triol, 8 ml. of pyridine, and 4 ml. of acetic anhydride was stirred at 0° C. for 1 hr and at 25° C. for 17 hr. The mixture was diluted with 10 ml. of methanol at 0° C. and evaporated to dryness. The residue was then dissolved in methylene chloride. This solution was washed with 10% aqueous sulfuric acid and saturated sodium bicarbonate solution. The organic phase was dried over anhydrous magnesium sulfate, filtered, and evaporated to dryness to yield [1α,3β,24S]-24-fluorocholest-5-en-1,3,25-triol 1,3-diacetate.

EXAMPLE 32

A mixture of 0.520 g. (0.0010 mole) of [1α,3β,24R]-24-fluorocholest-5-en-1,3,25-triol 1,3-diacetate, 0.45 g. of sodium bicarbonate, 0.192 g. (0.00066 mole) of 1,3-dibromo-5,5-dimethylhydantoin and 25 ml. of hexane was heated at reflux (80° C.) for 1 hr and cooled. The mixture was filtered and the solids were triturated with hexane and filtered. The filtrates were evaporated to dryness to yield [1α,3β,7ξ,24R]-7-bromo-24-fluorocholest-5-en-1,3,25-triol 1,3-diacetate.

EXAMPLE 33

A mixture of 0.260 g. (0.0005 mole) of [1α,3β,24S]-24-fluorocholest-5-en-1,3,25-triol 1,3-diacetate, 0.25 g. of sodium bicarbonate, 0.096 g. (0.00033 mole) of 1,3-dibromo-5,5-dimethylhydantoin, and 13 ml. of hexane was heated at reflux (80° C.) for 1 hr and cooled. The mixture was filtered and the solids were triturated with hexane and filtered. The combined filtrates were evaporated to dryness to yield [1α,3β,7ξ,24S]-7-bromo-24-fluorocholest-5-en-1,3,25-triol 1,3-diacetate.

EXAMPLE 34

A mixture of 0.605 g. (0.0010 mole) of [1α,3β,7ξ,24R]-7-bromo-24-fluorocholest-5-en-1,3,25-triol 1,3-diacetate, 0.6 ml. of s-collidine and 18 ml. of xylene was heated at reflux (140° C.) for 0.5 hr and cooled. The mixture was diluted with 30 ml. of toluene. This solution was washed with 10% aqueous sulfuric acid, and saturated aqueous sodium bicarbonate solution. The organic phase was dried over anhydrous magnesium sulfate, filtered, and evaporated to dryness. The residue was purified by column chromatography on 0.06–0.20 mm silica gel to yield [1α,3β,24R]-24-fluorocholesta-5,7-dien-1,3,25-triol 1,3-diacetate, $[\alpha]_D^{23}-21°$ (c 0.5, CHCl$_3$).

EXAMPLE 35

A mixture of 0.300 g. (0.0005 mole) of [1α,3β,7ξ,24S]-7-bromo-24-fluorocholest-5-en-1,3,25-triol 1,3-diacetate, 0.3 ml. of s-collidine and 10 ml. of xylene was heated at reflux (140° C.) for 0.5 hr and cooled. The mixture was diluted with 20 ml. of toluene. This solution was washed with 10% aqueous sulfuric acid, and saturated sodium bicarbonate solution. The organic phase was dried over anhydrous magnesium sulfate, filtered, and evaporated to dryness. The residue was purified by column chromatography on 0.06–0.20 mm silica gel to yield [1α,3β,24S]-24-fluorocholesta-5,7-dien-1,3,25-triol 1,3-diacetate.

EXAMPLE 36

A mixture of 0.258 g. (0.0005 mole) of [1α,3β,24R]-24-fluorocholesta-5,7-dien-1,3,25-triol 1,3-diacetate in 40 ml. of hexane and 10 ml. of tetrahydrofuran was irradiated for 0.5 hr under argon at −5° C. using a 450 W Hanovia high pressure mercury lamp, cooled with a Vycor-glass cooling finger. The solution was evaporated to dryness and the residue was purified with a Waters Associates liquid chromatograph Model 202 using 4'×1" silica gel column and a 4:1 mixture of n-hexane-ethyl acetate as eluant to give [1α,3β,6Z,24R]-24-fluoro-9,10-secocholesta-5(10), 6,8-trien-1,3,25-triol 1,3-diacetate.

EXAMPLE 37

A mixture of 0.011 g. (0.00002 mole) of [1α,3β,24S]-24-fluorocholesta-5,7-dien-1,3,25-triol 1,3-diacetate in 8 ml. of 4:1 hexane-tetrahydrofuran was irradiated for 0.2 hr under argon at −5° C. using a 450 watt Hanovia high pressure mercury lamp, cooled with a Vycor-glass cooling finger. The solution was evaporated to dryness and the residue was purified with a Waters Associates liquid chromatograph Model 202 using a 1'×⅜" silica gel column and a 4:1 mixture of n-hexane-ethyl acetate as eluant to give [1α,3β,6Z,24S]-24-fluoro-9,10-secocholesta-5(10), 6,8-trien-1,3,25-triol 1,3-diacetate.

EXAMPLE 38

A solution of 0.125 g. (0.00024 mole) of [1α,3β,6Z,24R]-24-fluoro-9,10-secocholesta-5(10),6,8-trien-1,3,25-triol 1,3-diacetate, and 15 ml. of 1% potassium hydroxide in methanol was stirred at 0° C. for 4 hr. The mixture was neutralized to pH 7.5 with glacial acetic acid in methanol. The solution was then evaporated to dryness at 0° C. The residue was partitioned between ethyl acetate and water. The organic phase was washed with saturated brine and dried over anhydrous sodium sulfate. The mixture was filtered and evaporated to dryness to yield [1α,3β,6Z,24R]-24-fluoro-9,10-secocholesta-5(10),6,8-trien-1,3,25-triol.

EXAMPLE 39

A mixture of 2.6 mg. (0.005 mmole) of [1α,3β,6Z,24S]-24-fluoro-9,10-secocholesta-5(10),6,8-trien-1,3,25-triol 1,3-diacetate and 1 ml. of 1% potassium hydroxide in methanol was stirred at 0° C. for 4 hr. The mixture was neutralized to pH 7.5 with glacial acetic acid in methanol. The solution was then evaporated to dryness at 0° C. The residue was partitioned between ethyl acetate and water. The organic phase was washed with saturated brine and dried over anhydrous sodium sulfate. The mixture was filtered and evaporated to dryness to yield [1α,3β,6Z,24S]-24-fluoro-9,10-secocholesta-5(10),6,8-trien-1,3,25-triol.

EXAMPLE 40

A mixture of 0.104 g. (0.00024 mole) of [1α,3β,6Z,24R]-24-fluoro-9,10-secocholeta-5(10),6,8-trien-1,3,25-triol, and 18 ml. of p-dioxane was heated at reflux (100° C.) for 1 hr and cooled. The mixture was then evaporated to dryness. The residue was purified with a Waters Associates liquid chromatograph Model 202 using a 4'×1" silica gel column and 3:1 ethyl acetate-hexane as eluant to give [1α,3β,5Z,7E,24R]-24-fluoro-9,10-secocholesta-5,7,10(19)-trien-1,3,25-triol also known as 1α,25-dihydroxy-24R-fluorocholecalciferol, $[\alpha]_D^{23} + 68°$ (c 0.5, MeOH).

EXAMPLE 41

A mixture of 2.1 mg. (0.005 mmole) of [1α,3β,6Z,24S]-24-fluoro-9,10-secocholesta-5(10),6,8-trien-1,3,25-triol, and 1 ml. of dioxane was heated at reflux (100° C.) for 1 hr and cooled. The mixture was then evaporated to dryness. The residue was purified on a Waters Associates liquid chromatograph Model 202 using a 1'×⅜" silica gel column and 3:1 ethyl acetate-hexane as eluant to give [1α,3β,5Z,7E,24S]-24-fluoro-9,10-secocholesta-5,7,10(19)-trien-1,3,25-triol also known as 1α,25-dihydroxy-24S-fluorocholecalciferol, $[\alpha]_D^{23} + 45°$ (c 0.1, CH₃OH).

EXAMPLE 42

| Item | Ingredients | mg/capsule | | |
|---|---|---|---|---|
| 1. | 1α,25-dihydroxy-24 R-fluorocholecalciferol | 0.00010 | 0.00025 | 0.00050 |
| 2. | polyethylene glycol 400 (PEG 400) | 200.00 | 200.00 | 200.00 |
| 3. | butylated hydroxy anisole(BHA) | 0.100 | 0.100 | 0.100 |
| 4. | ascorbyl palmitate | 1.00 | 1.00 | 1.00 |

Procedure:
Dissolve items 1, 3 and 4 in item 2, under a blanket of nitrogen and encapsulate.

EXAMPLE 43

| | | | |
|---|---|---|---|
| 1. | 1α,25-dihydroxy-24-R fluorocholecalciferol | 0.10 mg | 0.50 mg |
| 2. | 95% ethanol - 5% water | 2.00 ml | 3.00 ml |

Procedure
Dissolve item 1 in item 2 under a blanket of nitrogen and inject intramuscularly.

We claim:
1. A compound of the formula

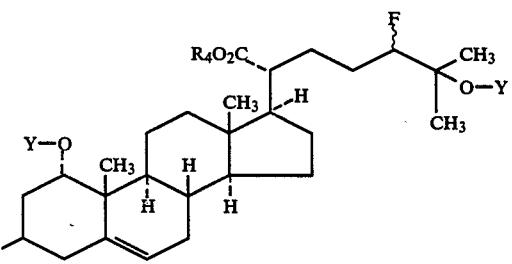

wherein R₄ is lower alkyl, phenyl, or substituted phenyl, F is fluoro and Y is a group of the formula $$R_3-O-\underset{\underset{R_2}{|}}{\overset{\overset{R_1}{|}}{C}}-$$

wherein $R_1$ is hydrogen or lower alkyl, $R_2$ and $R_3$ each taken independently are lower alkyl and $R_2$ and $R_3$ taken together are lower alkylene of from 3 to 6 carbons and the absolute configuration at C-24 is R or S or a R,S-mixture.

2. A compound of claim 1 where $R_4$ is lower alkyl and $R_1$ is hydrogen.

3. The compound of claim 2 which is [1α,3β,24R]-1,3-bis[(tetrahydro-2Hpyranyl)oxy]-(1-ethoxyethoxy)-24-fluorocholest-5-en-21-oic acid ethyl ester.

4. The compound of claim 2 which is [1α,3β,24S]-1,3-bis[(tetrahydro-2H-pyranyl)oxy]-(1-ethoxyethoxy)-24-fluorocholest-5-en-21-oic acid ethyl ester.

5. A compound of the formula wherein M is lithium, sodium, potassium, magnesium/2, or zinc/2, $R_4$ is lower alkyl, phenyl, or substituted phenyl and Y is a group of the formula $$R_3-O-\underset{\underset{R_2}{|}}{\overset{\overset{R_1}{|}}{C}}-$$

wherein $R_1$ is hydrogen or lower alkyl, $R_2$ or $R_3$ each taken independently are lower alkyl and $R_2$ and $R_3$ taken together are lower alkylene of from 3 to 6 carbon atoms.

6. The compound of claim 5 wherein M is lithium, sodium, or potassium, $R_4$ is lower alkyl and $R_1$ is hydrogen.

7. The compound of claim 6 which is the lithium enolate of [1α,3β]-1,3-bis[(tetrahydro-2H-pyran-2-yl)oxy]pregn-5-en-21-oic acid ethyl ester.

8. The compound of claim 6 which is the sodium enolate of [1α,3β]-1,3-bis[(tetrahydro-2H-pyran-2-yl)oxy]pregn-5-en-21-oic acid ethyl ester.

9. A compound of the formula wherein $R_4$ is lower alkyl, phenyl, or substituted phenyl, Y is a group of the formula $$R_3-O-\underset{\underset{R_2}{|}}{\overset{\overset{R_1}{|}}{C}}-$$

wherein $R_1$ is hydrogen or lower alkyl, $R_2$ or $R_3$ each taken independently are lower alkyl and $R_2$ and $R_3$ taken together are lower alkylene of from 3 to 6 carbon atoms.

10. The compound of claim 9 wherein $R_4$ is lower alkyl and $R_1$ is hydrogen.

11. The compound of claim 10 which is [1α,3β]-1,3-bis[(tetrahydro-2H-pyran-2-yl)oxy]pregn-5-en-21-oic acid ethyl ester.

12. A compound of the formula wherein F is fluoro and Y is a group of the formula $$R_3-O-\underset{\underset{R_2}{|}}{\overset{\overset{R_1}{|}}{C}}-$$

wherein $R_1$ is hydrogen or lower alkyl, $R_2$ and $R_3$ each taken independently are lower alkyl and $R_2$ and $R_3$ taken together are lower alkylene of from 3 to 6 carbon atoms and the absolute configuration at C-24 is R or S or a R,S-mixture.

13. The compound of claim 12 wherein $R_1$ is hydrogen.

14. The compound of claim 13 which is [1α,3β,24R]-1,3-bis-[(tetrahydro-2H-pyran-2-yl)oxy]-25-(1-ethoxyethoxy)-24-fluorocholest-5-en-21-ol.

15. The compound of claim 13 which is [1α,3β,24S]-1,3-bis-[(tetrahydro-2H-pyran-2-yl)oxy]-25-(1-ethoxyethoxy)-24-fluorocholest-5-en-21-ol.

16. A compound of the formula wherein X is iodo, bromo, chloro, lower alkylsulfonyloxy, phenylsulfonyloxy, or substituted phenylsulfonyloxy, F is fluoro, and Y is a group of the formula

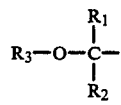

wherein R₁ is hydrogen or lower alkyl, R₂ and R₃ each taken independently are lower alkyl and R₂ and R₃ taken together are lower alkylene of from 3 to 6 carbon atoms and the absolute configuration at C-24 is R or S or a R,S-mixture.

17. The compound of claim 16 wherein X is iodo, bromo, lower alkylsulfonyloxy, phenylsulfonyloxy, or substituted phenylsulfonyloxy and R₁ is hydrogen.

18. The compound of claim 17 which is [1α,3β,24R]-1,3-bis[(tetrahydro-2H-pyran-2-yl)oxy]-25-(1-ethoxyethoxy)-24-fluorocholest-5-en-21-ol 21-(4-methylbenzenesulfonate).

19. The compound of claim 17 which is [1α,3β,24S]-1,3-bis[(tetrahydro-2H-pyran-2-yl)oxy]-25-(1-ethoxyethoxy)-24-fluorocholest-5-en-21-ol21-(4-methylbenzenesulfonate).

20. The compound of claim 17 which is [1α,3β,24R]-1,3-bis[(tetrahydro-2H-pyran-2-yl)oxy]-25-(1-ethoxyethoxy)-24-fluoro-21-iodocholest-5-ene.

21. The compound of claim 17 which is [1α,3β,24S]-1,3-bis[(tetrahydro-2H-pyran-2-yl)oxy]-25-(1-ethoxyethoxy)-24-fluoro-21-iodocholest-5-ene.

22. A compound of the formula

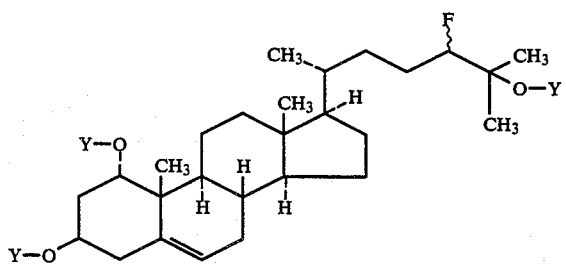

wherein F is fluoro and Y is a group of the formula

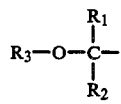

wherein R₁ is hydrogen or lower alkyl, R₂ and R₃ each taken independently are lower alkyl and R₂ and R₃ taken together are lower alkylene of from 3 to 6 carbon atoms and the absolute configuration at C-24 is R or S or a R,S-mixture.

23. The compound of claim 22 wherein R₁ is hydrogen.

24. The compound of claim 23 which is [1α,3β,24R]-1,3-bis[(tetrahydro-2H-pyran-2-yl)oxy]-25-(1-ethoxyethoxy)-24-fluorocholest-5-ene.

25. The compound of claim 23 which is [1α,3β,24S]-1,3-bis[(tetrahydro-2H-pyran-2-yl)oxy]-25-(1-ethoxyethoxy)-24-fluorocholest-5-ene.

26. A compound of the formula

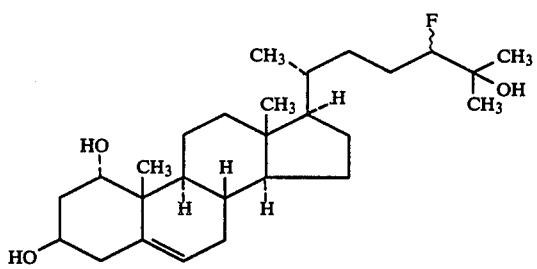

wherein F is fluoro and the absolute configuration at C-24 is R or S or a R,S-mixture.

27. The compound of claim 26 which is [1α,3β,24R]-24-fluorocholest-5-en-1,3,25-triol.

28. The compound of claim 26 which is [1α,3β,24S]-24-fluorocholest-5-en-1,3,25-triol.

29. A compound of the formula

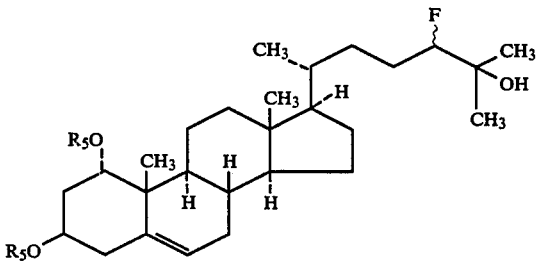

wherein R₅ is lower alkanoyl, F is fluoro, and the absolute configuration at C-24 is R or S or a R,S-mixture.

30. The compound of claim 29 which is [1α,3β,24R]-24-fluorocholest-5-en-1,3,25-triol 1,3-diacetate.

31. The compound of claim 29 which is [1α,3β,24S]-24-fluorocholest-5-en-1,3,25-triol 1,3-diacetate.

32. A compound of the formula

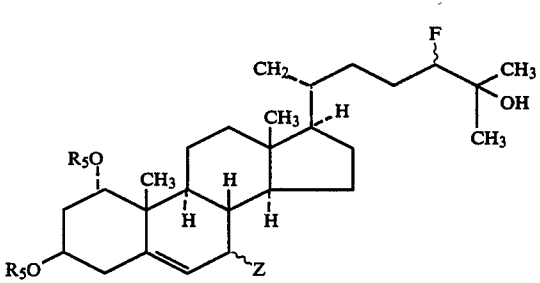

wherein R₅ is lower alkanoyl, Z is iodo, bromo or chloro, F is fluoro and the absolute configuration at C-24 is R or S or a R,S-mixture.

33. The compound of claim 32 wherein Z is iodo or bromo.

34. The compound of claim 33 which is [1α,3β,7ξ,24R]-7-bromo-24-fluorocholest-5-en-1,3,25-triol 1,3-diacetate.

35. The compound of claim 33 which is [1α,3β,7ξ,24S]-7-bromo-24-fluorocholest-5-en-1,3,25-triol 1,3-diacetate.

36. A compound of the formula

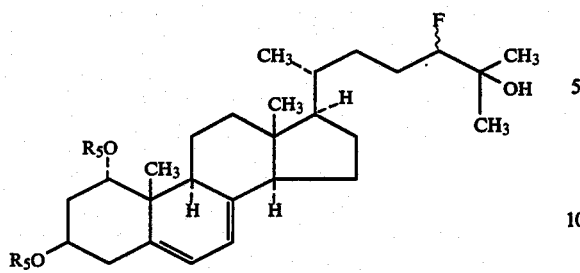

wherein $R_5$ is lower alkanoyl, F is fluorine and the absolute configuration at C-24 is R or S or a R,S-mixture.

37. The compound of claim 36 which is [1α,3β,24R]-24-fluorocholesta-5,7-diene-1,3,25-triol 1,3-diacetate.

38. The compound of claim 36 which is [1α,3β,24S]-24-fluorocholesta-5,7-diene-1,3,25-triol 1,3-diacetate.

39. A compound of the formula

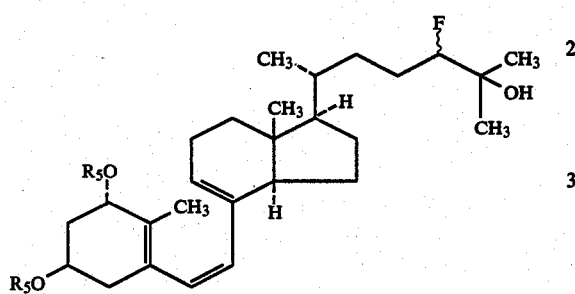

wherein $R_5$ is lower alkanoyl, F is fluorine and the absolute configuration at C-24 is R or S or a R,S-mixture.

40. The compound of claim 39 which is [1α,3β,6Z,24R]-24-fluoro-9,10-secocholesta-5(10),6,8-triene-1,3,25-triol 1,3-diacetate.

41. The compound of claim 39 which is [1α,3β,6Z,24S]-24-fluoro-9,10-secocholesta-5(10),6,8-triene-1,3,25-triol 1,3-diacetate.

42. A compound of the formula

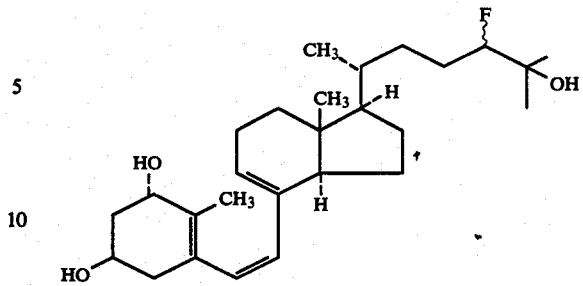

wherein F is fluoro and the absolute configuration at C-24 is R or S or a R,S-mixture.

43. The compound of claim 42 which is [1α,3β,6Z,24R]-24-fluoro-9,10-secocholesta-5(10),6,8-triene-1,3,25-triol.

44. The compound of claim 42 which is [1α,3β,6Z,24S]-24-fluoro-9,10-secocholesta-5(10),6,8-triene-1,3,25-triol.

45. A compound of the formula

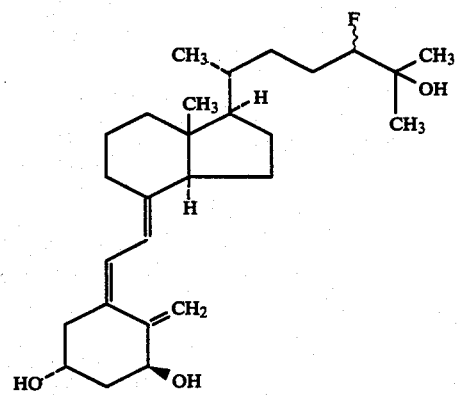

wherein F is fluorine and the absolute configuration at C-24 is R or S or a R,S-mixture.

46. The compound of claim 45 which is 1α,25-dihydroxy-24R-fluorocholecalciferol.

47. The compound of claim 45 which is 1α,25-dihydroxy-24S-fluorocholecalciferol.

* * * * *